United States Patent
Joshi et al.

(10) Patent No.: US 7,062,008 B2
(45) Date of Patent: *Jun. 13, 2006

(54) DETECTOR ASSEMBLY THERMAL MANAGEMENT SYSTEM AND METHOD

(75) Inventors: Ashutosh Joshi, Bangalore (IN); William Edward Burdick, Jr., Schenectady, NY (US); Sandeep Shrikant Tonapi, Niskayuna, NY (US); Joseph Lacey, Cambridge, WI (US)

(73) Assignee: General Electric Company, Niskayuna, NY (US)

( * ) Notice: Subject to any disclaimer, the term of this patent is extended or adjusted under 35 U.S.C. 154(b) by 42 days.

This patent is subject to a terminal disclaimer.

(21) Appl. No.: 10/610,163

(22) Filed: Jun. 30, 2003

(65) Prior Publication Data

US 2004/0264632 A1    Dec. 30, 2004

(51) Int. Cl.
*G01T 1/00* (2006.01)
(52) U.S. Cl. .................... 378/19; 250/370.09
(58) Field of Classification Search ............ 378/19, 378/4, 98.8; 250/363.05, 570.09, 363.02, 250/370.15, 370.09; 438/122
See application file for complete search history.

(56) References Cited

U.S. PATENT DOCUMENTS

| | | | | |
|---|---|---|---|---|
| 4,414,473 A | * | 11/1983 | Hoffman et al. | 250/370.09 |
| 5,248,885 A | * | 9/1993 | Sato et al. | 250/370.15 |
| 5,569,907 A | * | 10/1996 | Meunier | 250/208.1 |
| 5,857,007 A | | 1/1999 | Haq et al. | 378/19 |
| 6,357,515 B1 | * | 3/2002 | Bhatia | 165/80.3 |
| 6,510,195 B1 | * | 1/2003 | Chappo et al. | 378/19 |
| 6,621,084 B1 | * | 9/2003 | Wainer et al. | 250/370.09 |
| 6,658,082 B1 | * | 12/2003 | Okumura et al. | 378/19 |
| 2002/0054659 A1 | | 5/2002 | Okumara et al. | 378/3 |

* cited by examiner

*Primary Examiner*—David V. Bruce
*Assistant Examiner*—Hoon Song
(74) *Attorney, Agent, or Firm*—Fletcher Yoder

(57) ABSTRACT

A computed tomography (CT) system comprises an X-ray radiation source to project a plurality of X-ray beams through an object. A detector array comprises a plurality of detector assemblies. A gantry secured to the X-ray radiation source and the detector array rotates around a longitudinal axis. Further, each of the detector assembly comprises a detector subassembly adapted to detect the X-ray beams. These detector subassemblies are further adapted to convert the X-ray beams to a plurality of electrical signals. At least one circuit board assembly is coupled to the detector subassembly. The circuit board assembly typically comprises an integrated circuit array, such as, data acquisition chip array to acquire data corresponding to the electrical signals. The integrated circuit array further comprises a plurality of integrated circuit chips, for example, data acquisition chips mounted on at least one printed circuit board. A thermal management system is adapted for thermal communication between the data acquisition chip array and a heat sink assembly to control the thermal environment of each detector assembly. A processor is typically configured to process the electrical signals to generate a plurality of projection measurements. The processor is further adapted to perform computations on the projection measurements to construct an image of the object therefrom.

28 Claims, 10 Drawing Sheets

DETECTOR ASSEMBLY THERMAL MANAGEMENT SYSTEM AND METHOD

BACKGROUND OF THE INVENTION

The present invention relates generally to the field of computed tomography scanning systems and more particularly to thermal management of such computed tomography scanning systems.

Generally, a computed tomography (CT) scanning system for acquiring and processing image data of an object of interest, for example, a human patient, includes a source of X-ray radiation, typically an X-ray tube. A rotational system, typically including a gantry fixedly attached to the X-ray source and the detector array enables them to rotate at least one full 360° turn around the human patient.

Operationally, the X-ray radiation source projects the X-ray beam towards the object being imaged and further towards a detector array made up of a plurality of detector assemblies. The detector assemblies detect the X-ray radiation after passing through or around the object, and subsequently convert this X-ray radiation to a plurality of electrical signals. Further, as the X-ray radiation source and the detector array secured to the gantry rotate, an integrated circuit array, for example, a data acquisition chip array having a plurality of integrated circuits, such as, data acquisition chips mounted on a printed circuit board of each detector assembly collect data corresponding to electrical signals representing attenuation of the incident X-ray radiation after passing through or around the object. During operation, thermal energy is generated by the data acquisition chips as they are powered, to complete their processing functions. A particular challenge in such systems then arises from the need to remove this thermal energy from the chips and reduce the temperature variation between separate chips or processing circuits to the extent possible.

Improved versions of CT scanning systems are generally adapted to accommodate wider coverage of the patient. Therefore, the width of the improved detector assemblies of such improved CT scanning systems is desirably larger compared to conventional CT scanning systems. Accordingly, those improved detector assemblies are more densely populated with data acquisition chips than conventional detector assemblies for generating substantially large number of pixels from those improved CT scanning systems to accommodate the wider patient coverage. Hence, the thermal load released from the data acquisition chips of those improved detector assemblies is significantly higher compared to the thermal load released from detector assemblies of conventional CT systems.

Generally, in conventional approaches, the thermal load released from the detector assemblies of conventional CT systems is mitigated via direct convective cooling systems, for example, an air circulating system that blows coolant, such as, air over the data acquisition chip array. It may be appreciated that, such conventional direct convective cooling systems are generally inefficient towards dissipating the substantial thermal load released from the improved detector assemblies, because uniform thermal energy dissipation from all of these data acquisition chips constructing the improved detector assemblies cannot be addressed by relying on those direct convective cooling systems. More particularly, the thermal energy dissipation rate from the data acquisition chips positioned downstream of the direct convective coolant flow path is much less compared to thermal energy dissipation rate of other data acquisition chips (i.e. data acquisition chips positioned upstream of the direct convective coolant flow path). This non-uniform thermal energy dissipation rate from the data acquisition chips poses substantial risk of generating localized thermal hot spots at various locations of the improved detector assemblies that may throw out of gear overall control on the thermal environment thereof.

Accordingly, there is a need in the related art for an improved thermal management system that efficiently implements a method for controlling thermal environment of such improved detector assemblies in order to address effective mitigation of the excess thermal load generated therefrom.

BRIEF DESCRIPTION OF THE INVENTION

The present technique provides this controlled thermal environment to respond to such needs. Briefly, in accordance with some aspects of the present technique, a computed tomography (CT) system comprises an X-ray radiation source to project a plurality of X-ray beams through an object. A detector array comprises a plurality of detector assemblies. A gantry secured to the X-ray radiation source and the detector array rotates around a longitudinal axis. Further, each of the detector assembly comprises a detector subassembly adapted to detect the X-ray beams. These detector subassemblies are further adapted to convert the X-ray beams to a plurality of electrical signals. At least one circuit board assembly is coupled to the detector subassembly. The circuit board assembly typically comprises an integrated circuit array, for example, a data acquisition chip array to acquire data corresponding to the electrical signals. The integrated circuit array further comprises a plurality of integrated circuits, such as, data acquisition chips mounted on at least one printed circuit board. A thermal management system is adapted for thermal communication between the data acquisition chip array and a heat sink assembly to control the thermal environment of each detector assembly. A processor is typically configured to process the electrical signals to generate a plurality of projection measurements. The processor is further adapted to perform computations on the projection measurements to construct an image of the object therefrom. The present invention also provides a detector assembly and CT system incorporating the thermal management system as discussed before.

A method embodiment for controlling thermal environment of a detector assembly of a computed tomography system comprises a first step of detecting a plurality of X-ray beams emitted from an X-ray radiation source by a detector subassembly. At a next step, the method comprises converting at least a portion of the X-ray beams to a plurality of electrical signals by the detector subassembly. The method further comprises acquiring the electrical signals by a data acquisition chip array and subsequent capturing of data corresponding to these electrical signals by this data acquisition chip array. At a next step, the method includes generating thermal energy from this data acquisition chip array that is configured to be powered to perform processing of the electrical signals. The method further includes transporting the thermal energy from the data acquisition chip array to a heat sink assembly by a thermal link assembly. At a final step, the method comprises-dissipating the thermal energy transported to the heat sink assembly by a heat dissipation system.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
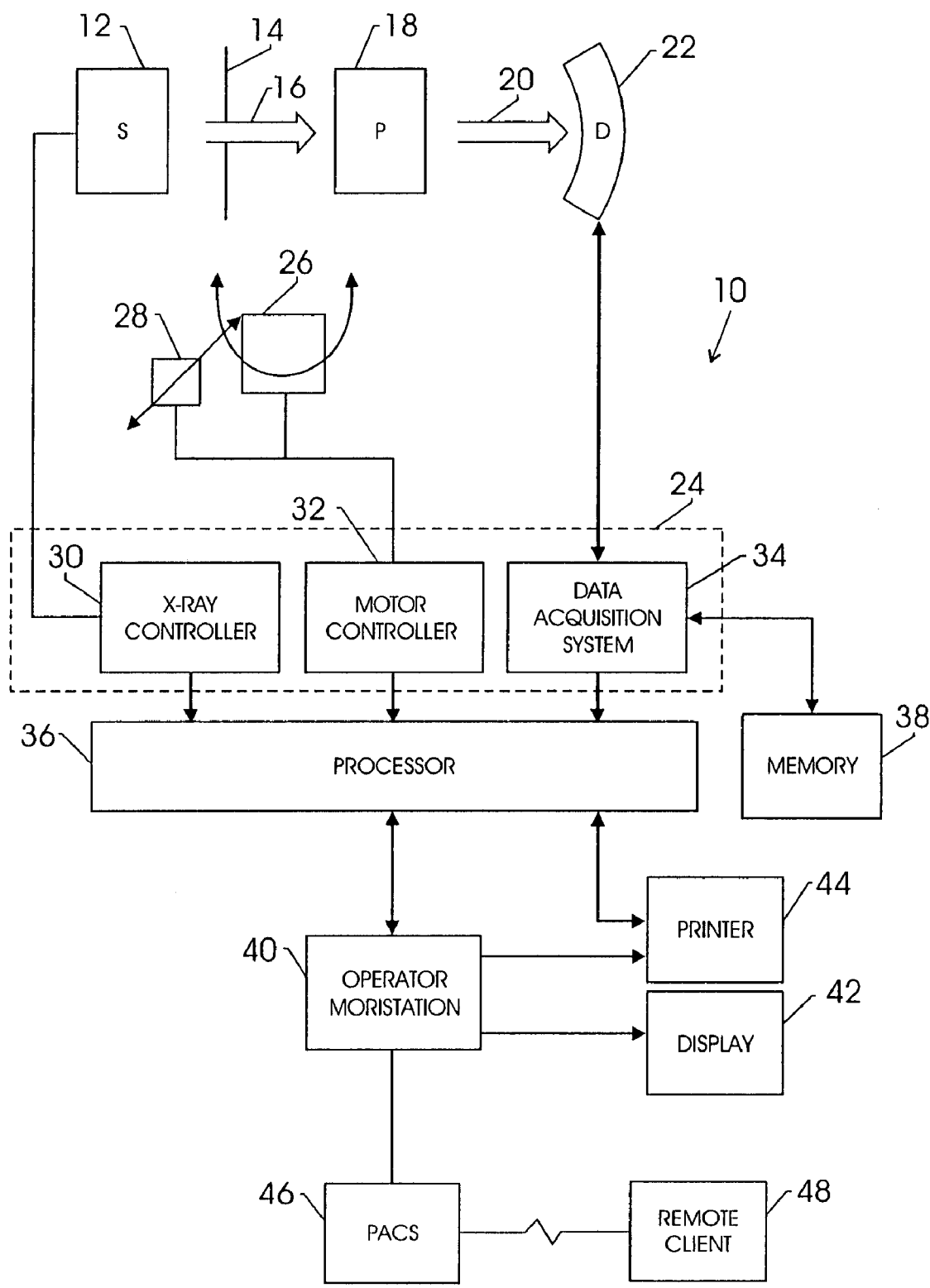
FIG. 1 is a diagrammatical view of an exemplary imaging system in the form of a CT imaging system for use in producing processed images in accordance with aspects of the present technique.

A computed tomography (hereinafter "CT") system generally helps in radiographic imaging of patients to aid clinical diagnosis by constructing an image of internal anatomical features of the patients. Such systems may also serve for imaging outside the medical field, where images are generated of any object of interest. FIG. 1 generally illustrates a diagrammatical view of such a computed tomography (hereinafter "CT") system 10 for acquiring and processing image data. More particularly, the CT system 10 acquires original image data, and further processes the image data for subsequent display and analysis. Turning now to the drawings, FIG. 1 illustrates diagrammatically the CT system 10 for acquiring and processing image data. The CT system 10 includes a source of X-ray radiation 12 positioned adjacent to a collimator 14. In this exemplary embodiment, the X-ray radiation source 12 is typically an X-ray tube.

The collimator 14 permits an incident X-ray beam 16 to pass into a region in which an object, such as a human patient 18, is positioned. A portion of the radiation 16 passes through or around the object 18 and subsequently the radiation 20 impacts a detector array, represented generally by reference numeral 22. Operationally, the detector array 22 detects the X-ray beams 16, 20 and subsequently converts this X-ray radiation to a plurality of electrical signals that represent the relative intensity of the incident X-ray beams 16. These electrical signals are acquired and processed further to construct an image of the features within the object, for example, the human patient 18.

The X-ray radiation source 12 is controlled by a system controller 24 that furnishes both power and control signals for CT examination sequences. Moreover, the detector array 22 coupled to the system controller 24 commands acquisition of the electrical signals generated in the detector array 22. In general, the system controller 24 commands operation of the imaging system to execute examination protocols and to process acquired data. Further, referring to FIG. 1, the system controller 24 is coupled to a linear positioning subsystem 26 and a rotational subsystem 28. The rotational subsystem 28 enables the X-ray source 12, the collimator 14 and the detector array 22 to be rotated at least one full 360° turn around the patient 18. It should be noted that, the rotational subsystem 28 typically includes a gantry 54 secured to the X-ray radiation source 12 and the detector array 22 (see FIG. 2). Thus, the system controller 24 may be utilized to operate the gantry 54 typically around a longitudinal axis. The linear positioning subsystem 26 enables the patient 18, or more specifically a patient table 58, to be displaced linearly. Further, the patient table 58 may be linearly moved within the gantry 54 to generate images of target areas of the object 18.

Additionally, as may be appreciated by those skilled in the art that, the source of X-ray radiation 12 may be controlled by an X-ray controller 30 disposed within the system controller 24. A motor controller 32 may be utilized to control the movement of the rotational subsystem 28 and the linear positioning subsystem 26. Further, the system controller 24 also comprises a data acquisition system 34. Typically, the detector array 22 is coupled to the system controller 24 and more particularly to the data acquisition system 34. The data acquisition system 34 receives data collected by plurality of electronic circuits constructing the detector array 22 architecture. In operation, the data acquisition system 34 receives sampled analog signals from the detector array 22 and converts them to digital signals for subsequent processing by a processor 36, typically a computer.

Operationally, the processor 36 is coupled to the system controller 24. The data collected by the data acquisition system 34 may be transmitted to the processor 36 and moreover, to a memory 38. It should be understood that any type of memory that stores a large amount of data might be utilized by the exemplary CT system 10. The memory 38 may include remote components for storing data, processing parameters and storing pre-determined instructions in form of computer programs. In addition, the processor 36 is configured to receive commands and scanning parameter inputs from an operator via an operator workstation 40 typically equipped with a keyboard and other input devices. Thus, the operator may observe the constructed image and other data relevant to the system from the computer 36, initiate imaging, and so forth.

A display 42 coupled to the operator workstation 40 may be utilized to observe the constructed image and to control imaging process. Additionally, the scanned image may be printed by a printer 44, typically coupled to the operator workstation 40. The display 42 and printer 44 may also be connected to the processor 36, either directly or via the operator workstation 40. Further, the operator workstation 40 may also be coupled to a picture archiving and communications system (hereinafter "PACS") 46. It should be noted that, PACS 46 might be coupled to a remote system 48 including, without limitation, radiology department information system (hereinafter "RIS"), hospital information system (hereinafter "HIS") via an internal or an external network, so that users at different locations may gain access to the image and the image data.

Figure 2:
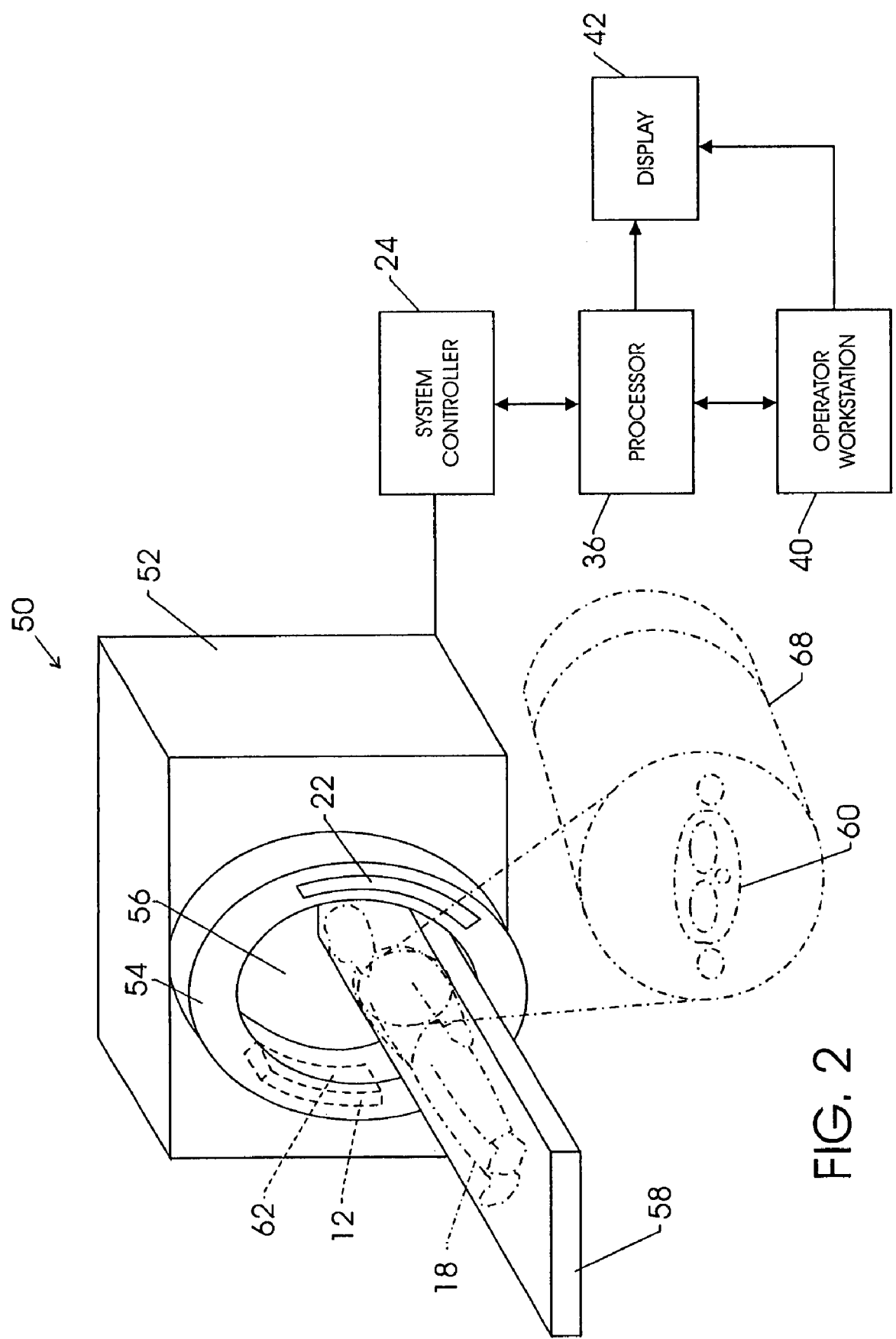
FIG. 2 is diagrammatical view of an exemplary physical implementation of the CT system of FIG. 1.

Referring generally to FIG. 2, an exemplary imaging system utilized in embodiments of the present technique may be a CT scanning system 50. The exemplary CT scanning system 50 in accordance with aspects of the present technique offers a wider patient coverage, relatively higher gantry speed and finer spatial resolution compared to conventional CT scanning systems.

Figure 3:
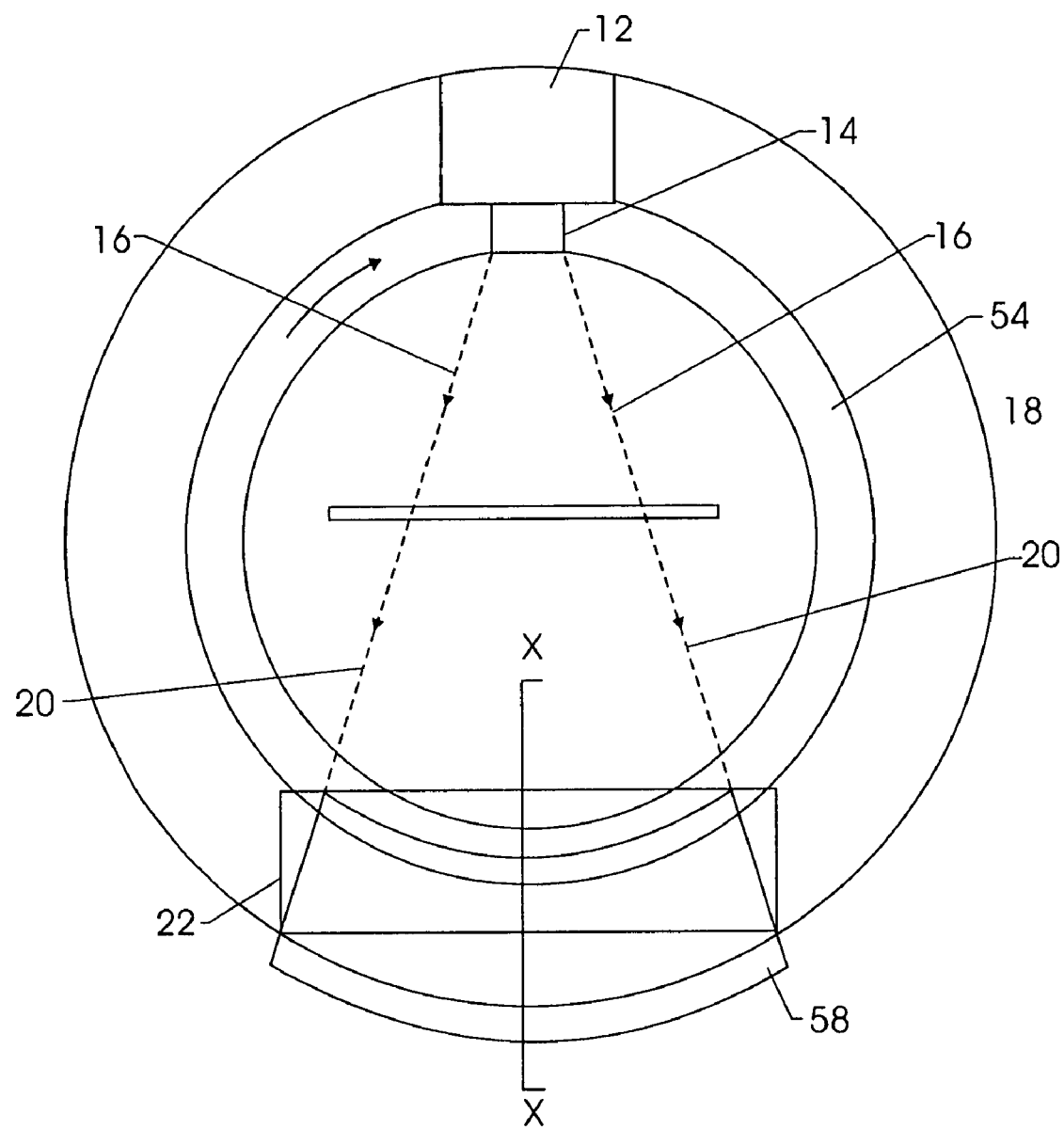
FIG. 3 is a representation of certain of the subsystems of the CT system of FIG. 2, including a radiation source and a detector array for receiving radiation during imaging sequences.
Figure 4:
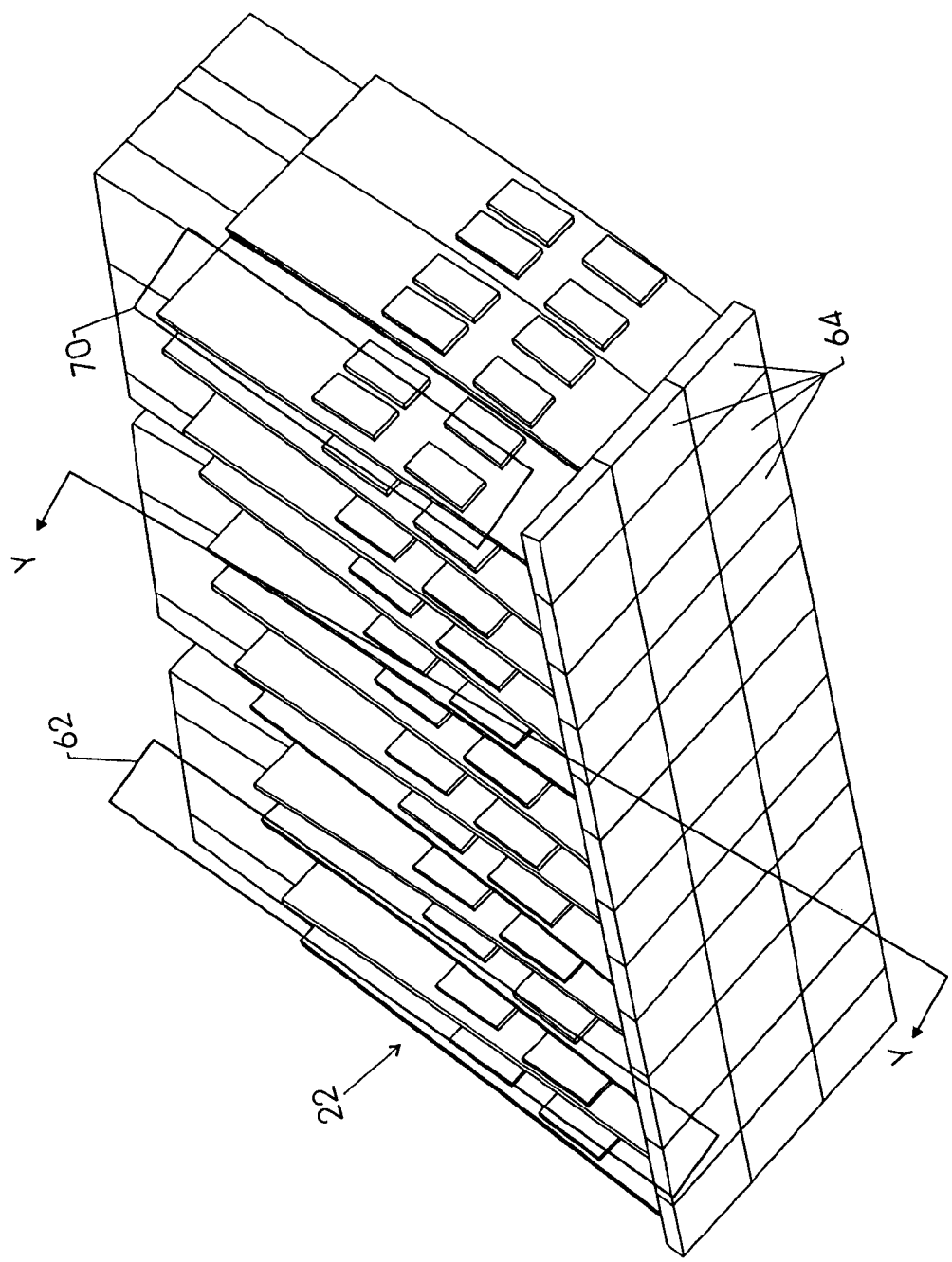
FIG. 4 is a perspective view of series of detector assemblies used in the detector array of FIG. 3, showing an exemplary arrangement of a plurality of detector circuits comprising the detector assembly.
Figure 5:
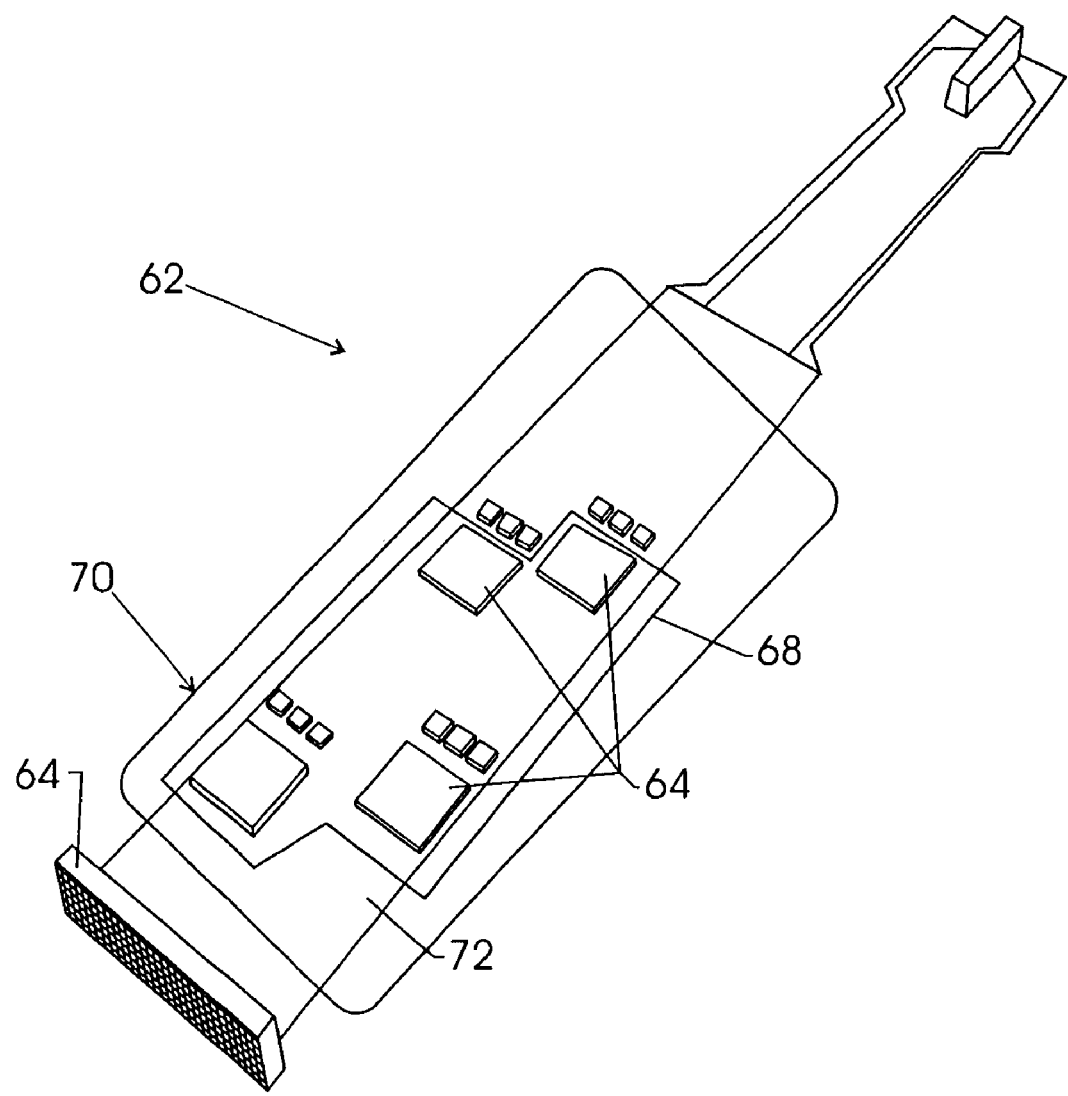
FIG. 5 is a perspective view of an exemplary circuit board assembly FIG. 4, depicting typical constructional aspects of a single detector circuit in accordance with the present technique.

FIG. 3 depicts certain subsystems of the CT scanning system to illustrate typical operation of thereof. Operationally, the X-ray radiation source 12 projects the X-ray beam 16 towards the object 18, and further towards the detector array 22. As discussed in preceding paragraphs, a portion of the incident X-ray beam 16 passes through or around the object 18 and subsequently a portion of the incident X-ray beam 16 including the attenuated X-ray beam 20 impinges on the detector array 22. An exemplary arrangement of the detector array 22 comprising a plurality of detector assemblies 62 is shown in FIG. 4. Further, FIG. 5 shows typical constructional aspects of each detector assembly 62 in accordance with the present technique. Typically, each of these detector assemblies 62 include a detector subassembly 64 and at least one circuit board assembly 70 that is coupled to the detector subassembly 64 using flexible materials, for example, Kapton.

From constructional perspective, each detector subassembly 64 further includes a plurality of solid-state detectors and photodiodes attached with each of these detectors (not shown). These solid-state detectors further include scintillating crystals that fluoresce when struck by X-ray beams to produce light energy therefrom. The photodiodes transform the light energy into a plurality of electrical signals. Referring to FIGS. 4 and 5, the detector subassembly 64 is adapted to detect the X-ray beams 16, 20 and further convert these X-ray beams to a plurality of electrical signals. The data corresponding to these electrical signals represents intensity of the X-ray beams 16, 20 at the position of the detector subassembly 64 at the time these X-ray radiations impinge thereon. These data are acquired by the circuit board assembly 70 that includes an integrated circuit array, for example, a data acquisition chip array 68 mounted on at least one printed circuit board 72. More particularly, as the X-ray radiation source 12 and the detector array 22 secured to the gantry 54 rotates, the integrated circuit array made up of the plurality of integrated circuits, such as, data acquisition chips 66 mounted on the printed circuit board 72 collect data corresponding to the electrical signals that represent attenuation of the incident X-ray beams 16 after passing through or around the object 18. The processor 36 coupled with the data acquisition system 34 is configured to process those data to generate a plurality of projection measurements and further perform computations on those projection measurements to construct an image 60 of the object 18.

It may be understood that, operationally, the thermal energy is generated from the data acquisition chips 66 as they are powered to perform their data processing function corresponding to the electrical signals acquired by them. It may further be noted that, the width of each of these detector assemblies 62 constructing the detector array 22 of the exemplary CT scanning system 50 recited in present technique, is generally larger than conventional CT scanning systems to facilitate accommodating wider coverage of the human patient 18. Accordingly, the thermal load generated from each of these data acquisition chips 66 of the detector assembly 62 is substantially higher compared to thermal load generated from detector assemblies of conventional CT systems. Typically, a thermal management system designed in accordance with aspects of present technique efficiently mitigates the excess thermal load generated from each of these detector assemblies 62. Generally, it may be appreciated from discussion in subsequent paragraphs that this thermal management system facilitates efficient control of the thermal environment of the detector assembly 62.

Figure 6:
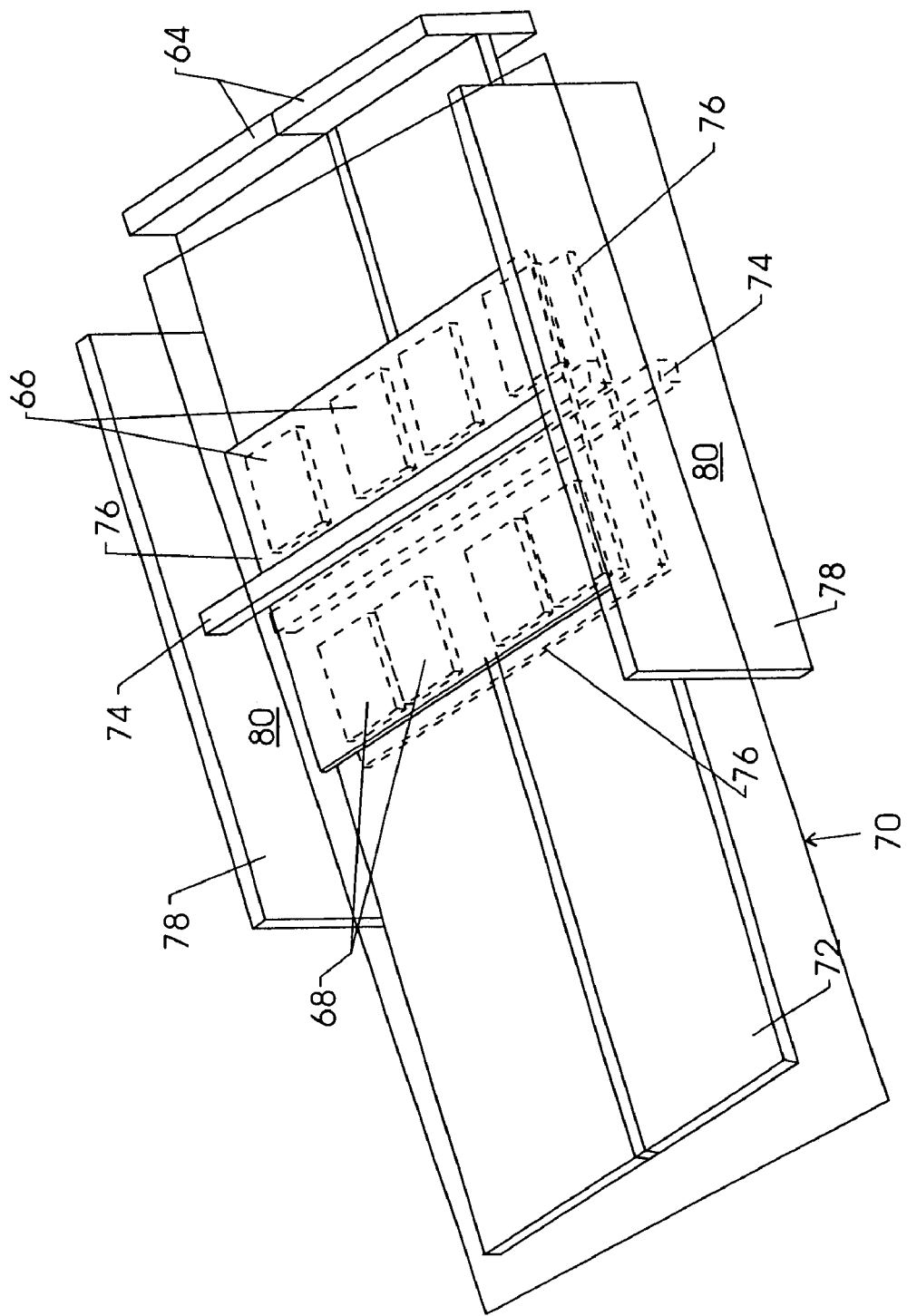
FIG. 6 is another perspective view of the exemplary circuit board assembly depicting details of an exemplary thermal management system in accordance with aspects of the present technique.

The thermal management system is depicted in greater detail in FIG. 6. In some embodiments, this thermal management system includes at least one spreader plate 76 disposed on the data acquisition chips 66 maintaining direct thermal contact therewith. These spreader plates 76 are generally fabricated from materials having substantially high thermal conductivity, for example, copper and aluminum. Further, these spreader plates are attached with the respective data acquisition chips 66 by typical thermally conductive adhesives or bonding agents. Operationally, the spreader plates 76 distribute the thermal energy generated by the data acquisition chip array 68 over the circuit board assembly 70 to enable substantially isothermal temperature distribution across entire detector assembly 62. As used herein, the term "substantially isothermal temperature distribution" means little or insignificant variation of temperature distribution across the detector assembly 62 components, such as, for example, the detector subassembly 64 and the circuit board assembly 70.

In present embodiment, the thermal management system also includes a thermal link assembly 74 adapted to transport excess thermal energy from the data acquisition chip array 68 to the heat sink assembly 80. Operationally, the thermal link assembly 74 is configured to provide a thermal energy transfer path offering minimum resistance to thermal communication between the data acquisition chip array 68 and the heat sink assembly 80.

In some embodiments, those thermal link assemblies 74 include at least one heat pipe. In operation, these heat pipes are typical "passive heat transfer devices" that are driven by thermal load of a typical heat source viz. the data acquisition chip array 68, so that thermal energy from this heat source (i.e. the data acquisition chip array 68) is transferred to the heat sink assembly 80 based upon two-phase heat transfer principles. Moreover, these heat pipes ensure minimum temperature drop across the thermal transfer path between the data acquisition chip array 68 and the heat sink assembly 80. Constructional aspects of each of these heat pipes include, a close evacuated chamber fabricated from a thermally conductive material, for example, copper. Further, inner surfaces of the chamber are lined with exemplary wick structures having capillary properties and these wick structures are saturated with a working fluid, typically having high latent heat of vaporization, such as chemical solvents, for example. Moreover, these working fluids are selected without compromising their desired compatibility with the heat pipe material. Thermal energy at a higher temperature end of the heat pipe (also referred as evaporator section) vaporizes the working fluid within portion of the wick structure exposed to the evaporator section. Further, the vaporized working fluid transfers its latent heat of vaporization to the heat sink assembly 80. The condensed working fluid is drawn back to the evaporator section of those heat pipes by capillary action of the wick structures.

It may be therefore appreciated that, the thermal link assembly 74 and the spreader plate 76 envisaged according to the present technique, beneficially ensures controlled thermal environment of the detector assembly 62 within pre-determined thermal specifications. Additionally, maintaining a steady-state thermal environment in the detector assembly 62 within such pre-determined thermal specifications desirably avoids thermal hot spot formation in localized areas thereof. Moreover, this efficiently controlled thermal environment provided by the thermal management system envisioned in current technique, ensures minimum thermal exposure of the typically thermally sensitive components of the detector assembly that are positioned in close proximity to the heat source viz. the integrated circuit array. As a further consequence thereof, system reliability of these CT scanning systems 50 as a whole is enhanced, while providing those desired thermal management benefits.

The heat sink assembly 80 further includes at least one heat dissipation system 78 that dissipates the thermal energy transported therein from the data acquisition chip array 68 via the thermal link assembly 74. In some embodiments, the heat dissipation system 78 depicted in FIG. 6 includes a plurality of exemplary fins 82 to construct a typical fin array (see FIG. 7 and FIG. 8). In operation, the thermal energy transported from the data acquisition chip array is generally dissipated by buoyancy-induced natural convective current of free-stream air or cooling fluid surrounding those fins 82. The thermal energy dissipation rate from those fins 82 depends on various factors, including without limitation, the surface area of those fins and the spacing between the consecutive fins, for example. It may be noted that, the surface area of those fins 82 may be adjusted by selecting their cross-sectional geometry from various configurations that include, but are not limited to, square-shaped geometry, rectangular-shaped geometry, circular-shaped geometry, elliptical-shaped geometry and irregular-shaped geometry. It may however be noted that the exemplary heat dissipation system may comprise any type of heat dissipation systems including, without limitation, heat exchangers and cooling baths constantly maintained at a substantially low temperature for example.

In implementation, determining the number of fins in the fin array, the cross-sectional geometry of those fins and the spacing between the consecutive fins depends upon such as, for example, thermal dissipation effectiveness of those fins, thermal load transported to those fins from the data acquisition chip array 68 and physical dimension or size limitations of the heat dissipation system 78. Operationally, the spacing between the consecutive fins is desirably maintained greater than a pre-determined value in order to avoid collapse of thermal boundary layers formed therebetween. It may be appreciated that, avoiding such collapse of thermal boundary layers between the consecutive fins desirably promotes efficient natural convective dissipation of the thermal load transferred therein from the data acquisition chip array 68. Moreover, increased population of the fins proportionately increases effective heat transfer area to enable enhanced dissipation of thermal energy therefrom. It may be noted that, as the number or population of fins 82 and the spacing between the consecutive fins increases, overall size of the heat dissipation system 78 becomes enlarged further, deteriorating its effectiveness for positioning them in a pre-determined space in the detector assembly 62 architecture.

Therefore, in order to strike a balance between thermal dissipation effectiveness and overall size of the heat dissipation system 78, in some embodiments, the natural convective thermal dissipation induced by the fins is supplemented with forced convective thermal dissipation induced by a typical air circulation system. Such air circulation system includes at least one air blower 84 disposed in at least one plenum chamber 94 (see FIG. 7 through FIG. 10).

Figure 7:
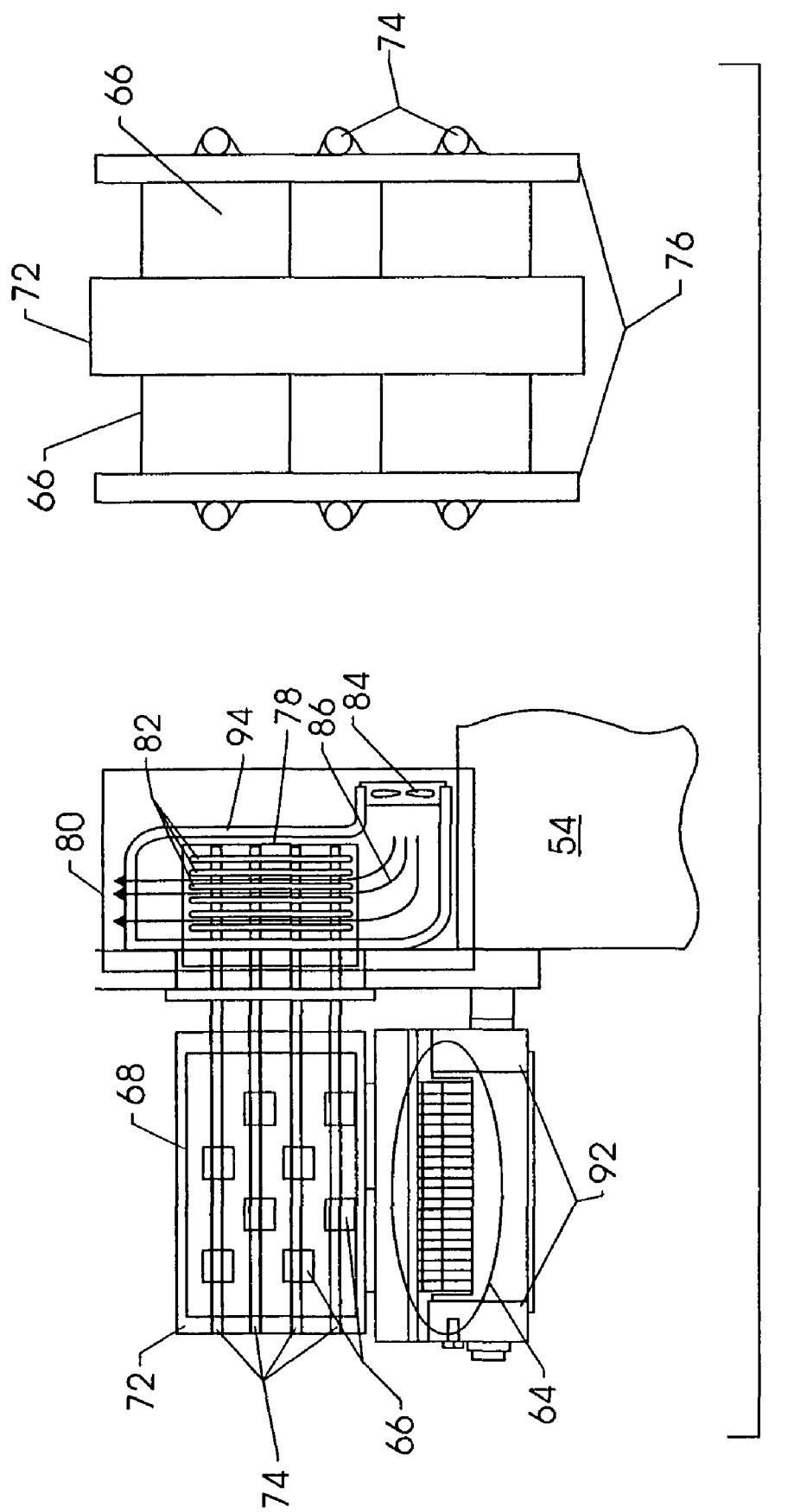
FIG. 7 includes plan and end views of the thermal management system of FIG. 6 depicting an embodiment thereof in accordance with aspects of the present technique.

Referring to FIG. 7, in one embodiment of the present technique, the thermal link assembly 74 includes a plurality of heat pipes disposed over the spreader plates 76. Therefore the thermal link assembly 74 in present embodiment maintains active thermal contact with the data acquisition chips 66 through the spreader plates 76. The heat pipes building the thermal link assembly 74 may be characterized as typical thermal mass adjacent to the heat source, viz. the data acquisition chip array 68. Such thermal mass maintaining active thermal contact with the data acquisition chip array 68 beneficially aids in relatively faster thermal response of the thermal link assembly 74 during transfer of thermal load from the data acquisition chip array 68 to the heat sink assembly 80. It may be noted that, significant quantum of thermal load is generated during transient thermal phenomenon in the exemplary CT scanning system 50, for example, startup of the X-ray source 12 power supply and the gantry 54 rotation. Such thermal load should desirably be dissipated fast enough to avoid further undesirable circumstances consequent to thermal energy build-up in the detector assembly. The thermal response provided by the thermal link assembly in present embodiment beneficially addresses such undesirable circumstances by quickly transferring the thermal load from the data acquisition chip array 68 to the heat sink assembly 80.

Figure 8:
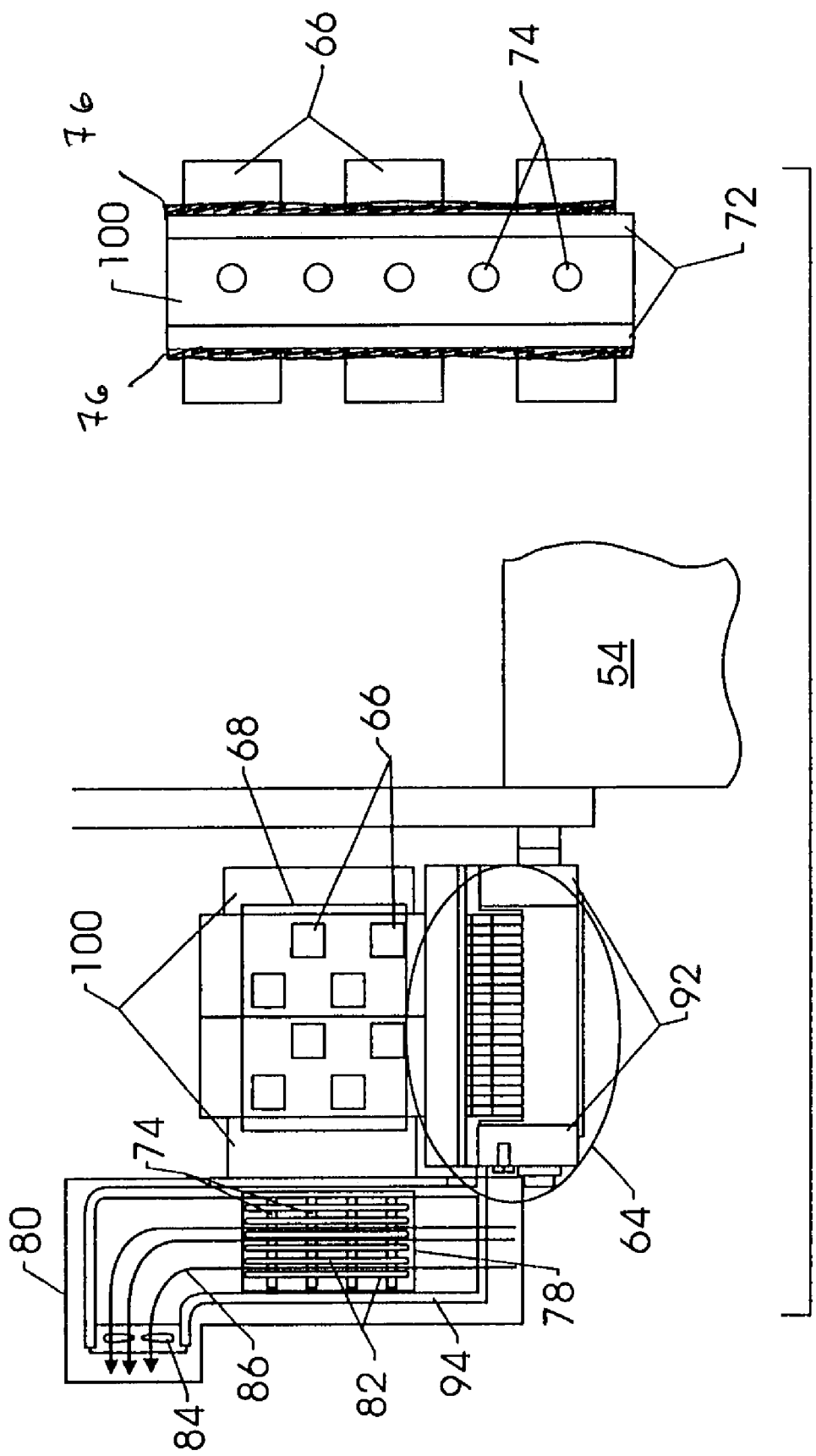
FIG. 8 includes plan and end views of the thermal management system of FIG. 6 depicting another embodiment thereof in accordance with aspects of the present technique.

Referring to another alternative embodiment depicted in FIG. 8, the thermal link assembly comprising a plurality of heat pipes is embedded in an exemplary metal core 100 disposed between a pair of printed circuit boards 72. Accordingly, in present embodiment, the thermal mass of the heat pipes constructing the thermal link assembly maintain passive or indirect thermal contact with the data acquisition chip array 68 via the metal core 100. It may however be appreciated that, although, in present embodiment, the thermal response of the thermal link assemblies is relatively slower compared to the thermal link assemblies that maintain active thermal contact with the data acquisition chips 66, those thermal link assemblies maintaining passive thermal contact with the data acquisition chip array typically help to maintain structural stability of the circuit board assembly 70. Such enhanced structural stability results due to transfer of a relatively small portion of the static and dynamic load of the thermal link assemblies 74 to the circuit board assembly 70.

Figure 9:
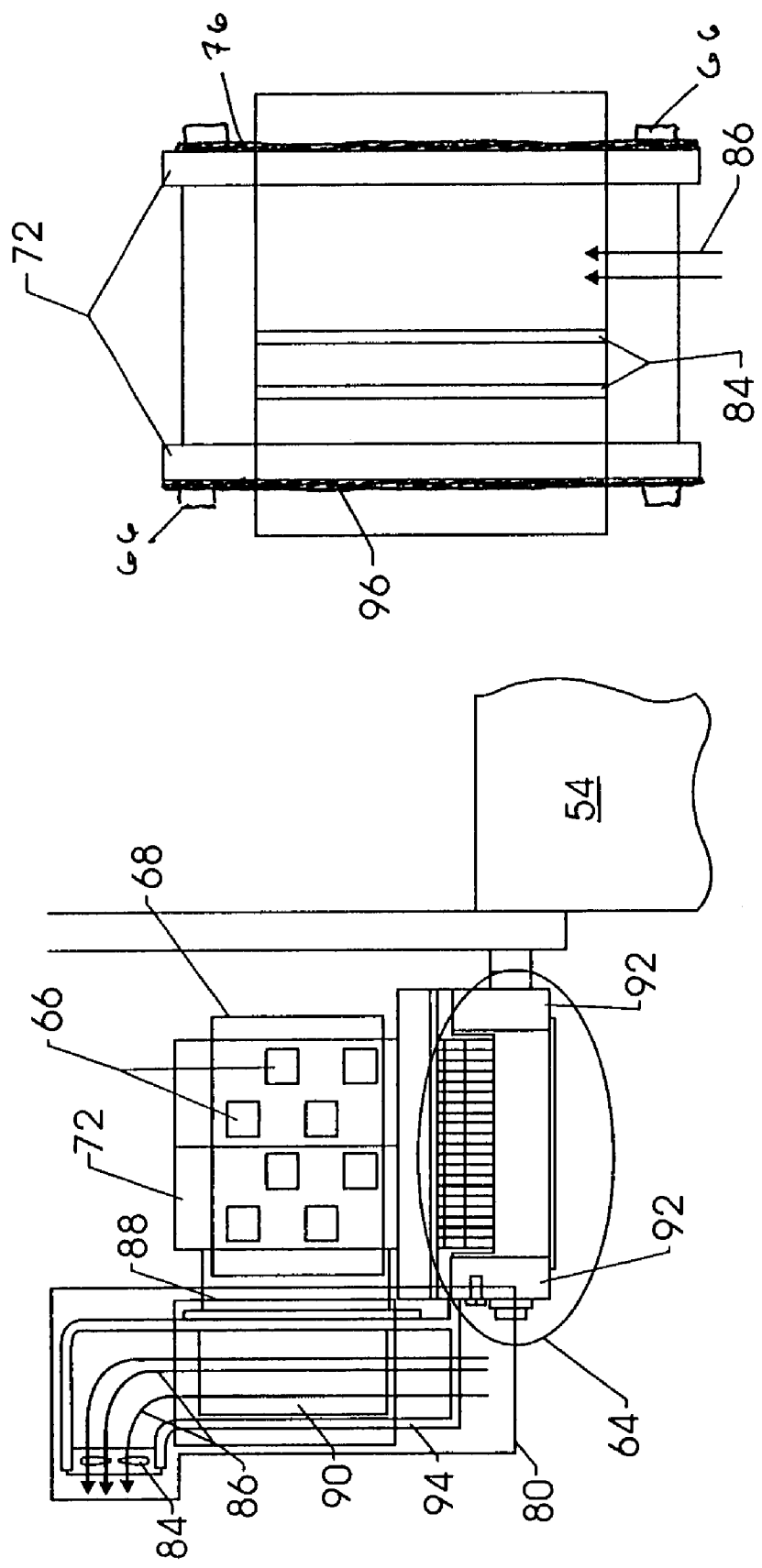
FIG. 9 includes plan and end views of the thermal management system of FIG. 6 depicting another embodiment thereof in accordance with aspects of the present technique.
Figure 10:
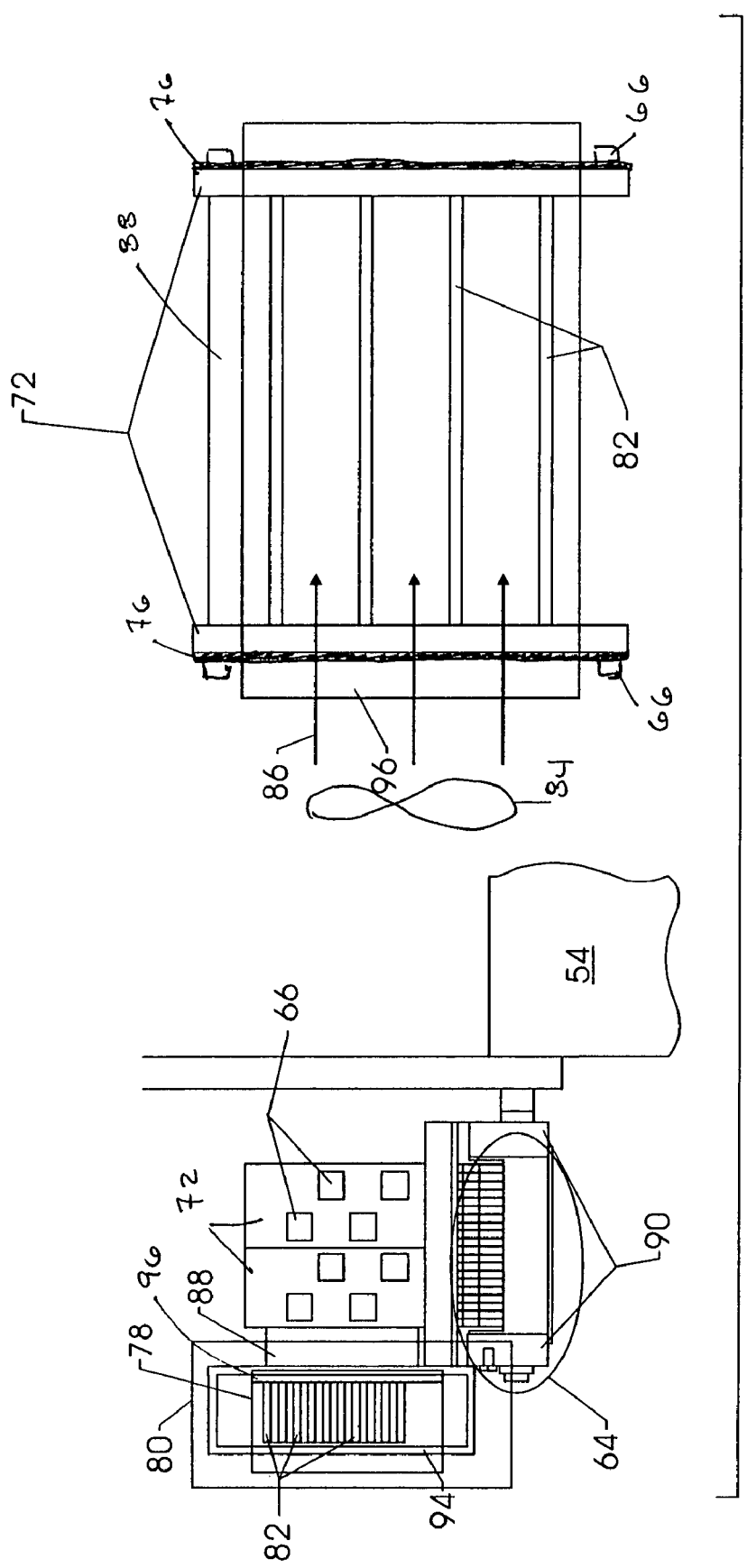
FIG. 10 includes plan and end views of the thermal management system of FIG. 6 depicting another embodiment thereof in accordance with aspects of the present technique.

In accordance with another alternative embodiment depicted in FIG. 9 and FIG. 10, the thermal link assembly includes at least one thermally conductive plate 88 extended from the circuit boards 72 and further disposed to maintain passive or indirect thermal contact with the data acquisition chip array 68 via those printed circuit boards 72. In some embodiments, exemplary plate-shaped fins 90 having rectangular or square-shaped cross-sectional geometry may be further extended from a typical bracket 96 configured to secure those thermally conductive plates 88. Functionally, those fins 90 dissipate the excess thermal load transferred therein from the data acquisition chip array 68 via the thermally conductive plates 88. The cross-sectional geometry of the fins 82, 90 may have any pre-determined geometrical shape in accordance with embodiments discussed before.

It may further be appreciated that, in some embodiments, the air blowers 84 constructing the air circulation system may be positioned in such a manner that the forced convective flow stream 86 from the heat dissipation system 78 is typically along a longitudinal direction (see FIG. 7 through FIG. 9). In some alternative embodiments, this flow stream 86 may be along a lateral direction (see FIG. 10). The forced convective flow stream direction 86 or more particularly, positioning of the air blowers 84 generally depends on constructional architecture of the detector assembly 62 that might impose limitation on positioning these air blowers 84 in the detector assemblies 62.

Further, a method according to the present technique includes a method for controlling thermal environment of the detector assembly 62 of the CT scanning system 50. This method further includes a first step of detecting the plurality of X-ray beams 16, 20 emitted from the X-ray radiation source 12 by a detector subassembly 64. At a subsequent step, at least a portion of these X-ray beams 16, 20 are converted to a plurality of electrical signals by the detector subassembly 64. Further, these electrical signals are acquired by the data acquisition chip array 68 comprising a plurality of data acquisition chips 66. Subsequently, this data acquisition chip array 68 captures data corresponding to those electrical signals. At a further step, thermal energy is released from the data acquisition chip array that is powered to perform processing of the electrical signals. Next, this thermal energy released from the data acquisition chip array 68 is transported to the heat sink assembly 80 through the thermal link assembly 74. Final step of the method expression includes dissipating the thermal energy transported to the heat sink assembly 80 from the data acquisition chip array 68 by the heat dissipating system 78. The aspects characterizing various alternative embodiments of the thermal management system of the detector assembly 62 in accordance with this method are identical to those aspects discussed in preceding paragraphs.

While the invention may be susceptible to various modifications and alternative forms, specific embodiments have been shown by way of example in the drawings and have been described in detail herein. However, it should be understood that the invention is not intended to be limited to the particular forms disclosed. Typically, the thermal management system envisioned in accordance with the present technique may as well be utilized in electronic circuits for other systems including medical imaging systems, such as, X-ray imaging system and magnetic resonance imaging system, for example. Accordingly, the invention in its present form is intended to cover all modifications, equivalents, and alternatives falling within the spirit and scope thereof as defined by the following appended claims.

What is claimed is:

1. A computed tomography system comprising:
a gantry configured to rotate around a longitudinal axis;
an X-ray radiation source secured to the gantry and configured to project a plurality of X-ray beams through an object;
a detector array comprising a plurality of detector assemblies; each detector assembly further comprising:
a detector subassembly adapted to detect the X-ray beams and further adapted to convert at least a portion of the X-ray beams to a plurality of electrical signals; and at least one circuit board assembly coupled to the detector subassembly;
each circuit board assembly comprising an integrated circuit array to acquire data corresponding to the electrical signals; the integrated circuit array further comprising a plurality of integrated circuits mounted on at least one printed circuit board and a thermal management system adapted for thermal communication between the integrated circuit array and a heat sink assembly to enable substantially isothermal temperature distribution across the detector assembly; and
a processor configured to generate a plurality of projection measurements from the electrical signals; wherein the processor is further configured to perform computations on the projection measurements to construct an image of the object therefrom.

2. The computed tomography system of claim 1, wherein the thermal management system further comprises at least one spreader plate disposed to maintain direct thermal contact with the integrated circuit array for substantially isothermal distribution of the thermal energy generated from the integrated circuit array across the detector assembly.

3. The computed tomography system of claim 2, wherein the thermal management system further comprises a thermal link assembly adapted to transport thermal energy from the integrated circuit array to the heat sink assembly.

4. The computed tomography system of claim 3, wherein the thermal link assembly comprises at least one heat pipe disposed to maintain active thermal contact with the integrated circuit array.

5. The computed tomography system of claim 3, wherein the thermal link assembly comprises at least one heat pipe disposed to maintain passive thermal contact with the integrated circuit array.

6. The computed tomography system of claim 3, wherein the thermal link assembly comprises at least one thermally conductive plate disposed to maintain passive thermal contact with the integrated circuit array.

7. The computed tomography system of claim 3, wherein the heat sink assembly comprises at least one heat dissipation system adapted to dissipate the thermal energy transported therein from the integrated circuit array.

8. The computed tomography system of claim 7, wherein the heat dissipation system comprises a plurality of fins adapted to perform free convective dissipation of the thermal energy transported therein from the integrated circuit array.

9. The computed tomography system of claim 8, wherein each of the fins have a cross-sectional geometry selected from the group consisting of square-shaped geometry, rectangular-shaped geometry, circular-shaped geometry, elliptical-shaped geometry and irregular-shaped geometry.

10. The computed tomography system of claim 8, wherein the heat sink assembly further comprises an air circulation system adapted to perform forced convective dissipation of the thermal energy transported therein from the integrated circuit array.

11. The computed tomography system of claim 10, wherein the air circulation system comprises at least one air blower disposed in at least one plenum chamber.

12. A detector assembly of a computed tomography system comprising:
a detector subassembly adapted to detect a plurality of X-ray beams emitted from an X-ray radiation source and further adapted to convert at least a portion of the X-ray beams to a plurality of electrical signals; and
at least one circuit board assembly coupled to the detector subassembly; the circuit board assembly further comprising:

at least one printed circuit board;
a data acquisition chip array comprising a plurality of data acquisition chips mounted on the printed circuit board to acquire data corresponding to the electrical signals;
a heat sink assembly comprising a heat dissipation system and an air circulation system; and
a thermal management system adapted for thermal communication between the data acquisition chip array and the heat sink assembly to enable substantially isothermal temperature distribution across the detector assembly; the thermal management system comprising a thermal link assembly adapted to transport thermal energy from the data acquisition chip array to the heat sink assembly.

13. The detector assembly of claim 12, wherein the thermal link assembly comprises at least one heat pipe disposed to maintain active thermal contact with the data acquisition chip array.

14. The detector assembly of claim 12, wherein the thermal link assembly comprises at least one heat pipe disposed to maintain passive thermal contact with the data acquisition chip array.

15. The detector assembly of claim 12, wherein the thermal link assembly comprises at least one thermally conductive plate disposed to maintain passive thermal contact with the data acquisition chip array.

16. The detector assembly of claim 12, wherein the heat sink assembly comprises at least one heat dissipation system adapted to perform dissipation of the thermal energy transported therein from the data acquisition chip array.

17. The detector assembly of claim 16, wherein the heat dissipation system comprises a plurality of fins adapted to perform free convective dissipation of the thermal energy transported therein from the data acquisition chip array.

18. The detector assembly of claim 17, wherein each of the fins have a cross-sectional geometry selected from the group consisting of square-shaped geometry, rectangular-shaped geometry, circular-shaped geometry, elliptical-shaped geometry and irregular-shaped geometry.

19. The detector assembly of claim 16, wherein the heat sink assembly further comprises an air circulation system adapted to perform forced convective dissipation of the thermal energy transported therein from the data acquisition chip array.

20. The detector assembly of claim 19, wherein the air circulation system comprises at least one air blower disposed in at least one plenum chamber.

21. A method for controlling thermal environment of a detector assembly of a computed tomography system comprising:
detecting a plurality of X-ray beams emitted from an X-ray radiation source by a detector subassembly;
converting at least a portion of the X-ray beams to a plurality of electrical signals by the detector subassembly;
acquiring the electrical signals by a data acquisition chip array;
capturing data corresponding to the electrical signals by the data acquisition chip array;
generating thermal energy from the data acquisition chip array configured to be powered to perform data processing corresponding to the electrical signals;
transporting the thermal energy from the data acquisition chip array to a heat sink assembly by a thermal link assembly, wherein the transporting enables substantially isothermal temperature distribution across the detector assembly; and
dissipating the thermal energy transported to the heat sink assembly from the data acquisition chip array by a heat dissipation system.

22. The method of claim 21, wherein the thermal link assembly comprises at least one heat pipe disposed to maintain active thermal contact with the data acquisition chip array.

23. The method of claim 21, wherein the thermal link assembly comprises at least one heat pipe disposed to maintain passive thermal contact with the data acquisition chip array.

24. The method of claim 21, wherein the heat sink assembly comprises at least one heat dissipation system adapted to dissipate the thermal energy transferred therein from the data acquisition chip array.

25. The method of claim 24, wherein the heat dissipation system comprises a plurality of fins adapted to perform free convective dissipation of the thermal energy transported therein from the data acquisition chip array.

26. The method of claim 24, wherein the heat sink assembly further comprises an air circulation system adapted to perform forced convective dissipation of the thermal energy transported therein from the data acquisition chip array.

27. The method of claim 26, wherein the air circulation system comprises at least one air blower disposed in at least one plenum chamber.

28. A means for controlling thermal environment of a detector array of a computed tomography system comprising:
means for detecting a plurality of X-ray beams emitted from an X-ray radiation source;
means for converting at least a portion of the X-ray beams to a plurality of electrical signals;
means for acquiring the electrical signals;
means for capturing data corresponding to the electrical signals;
means for generating thermal energy from a data acquisition chip array configured to be powered to perform data processing corresponding to the electrical signals;
means for transporting the thermal energy from the data acquisition chip array to a heat sink assembly; wherein the means for transporting the thermal energy enables substantially isothermal temperature distribution across the detector array; and
means for dissipating the thermal energy transported to the heat sink assembly from the data acquisition chip array.

* * * * *